United States Patent
Lindo et al.

(10) Patent No.: US 12,186,140 B2
(45) Date of Patent: Jan. 7, 2025

(54) AREOLA MARKER PLACEMENT GUIDE

(71) Applicant: MEDSTAR HEALTH, INC., Columbia, MD (US)

(72) Inventors: Colleen Lindo, Baltimore, MD (US); Gabriel Del Corral, Baltimore, MD (US); Dae Capobianco Rodriguez, Austin, TX (US); Stephen Kinsey, Lutherville, MD (US)

(73) Assignee: MEDSTAR HEALTH, INC., Columbia, MD (US)

( * ) Notice: Subject to any disclaimer, the term of this patent is extended or adjusted under 35 U.S.C. 154(b) by 452 days.

(21) Appl. No.: 17/717,700

(22) Filed: Apr. 11, 2022

(65) Prior Publication Data

US 2022/0331057 A1 Oct. 20, 2022

Related U.S. Application Data

(60) Provisional application No. 63/176,592, filed on Apr. 19, 2021.

(51) Int. Cl.
*A61B 90/00* (2016.01)
(52) U.S. Cl.
CPC ...... *A61B 90/39* (2016.02); *A61B 2090/3908* (2016.02)
(58) Field of Classification Search
CPC .................................................... A61B 90/39
USPC ................... 33/511, 512, 574, 578; 600/587
See application file for complete search history.

(56) References Cited

U.S. PATENT DOCUMENTS

| | | | | |
|---|---|---|---|---|
| 2,245,350 A | * | 6/1941 | Marshall | A61M 5/427 604/116 |
| 2,559,501 A | * | 7/1951 | Fred | A61B 5/107 73/426 |
| 5,414,943 A | * | 5/1995 | Vogt | A61B 5/107 33/759 |
| 5,485,855 A | * | 1/1996 | Shiraiwa | A41H 1/02 600/587 |
| 5,499,989 A | * | 3/1996 | LaBash | A61B 17/3403 606/130 |
| 6,272,761 B1 | * | 8/2001 | Pechter | G01B 3/02 33/759 |
| 6,412,491 B1 | * | 7/2002 | Rusin | A61B 90/39 128/897 |
| 6,981,988 B1 | * | 1/2006 | Kinsley | A61F 2/12 623/7 |
| 7,127,826 B2 | * | 10/2006 | Russell | A61B 90/39 33/566 |

(Continued)

OTHER PUBLICATIONS

Accurate Surgical & Scientific Instruments Corporation "ASSI Oval Areola Marker", http://www.accuratesurgical.com/products/plastic-surgery-breast-surgery/product/4882-assi-oval-areola-marker, last accessed Sep. 12, 2022.

*Primary Examiner* — George B Bennett
(74) *Attorney, Agent, or Firm* — Tarolli, Sundheim, Covell & Tummino LLP

(57) ABSTRACT

An areola marker placement guide. A guide can include a superior anchor, an inferior anchor and a slidable housing located between the superior anchor and the inferior anchor. The guide can include vertical and horizontal telescoping assemblies with right and left areola markers connected to the horizontal telescoping assemblies. The guide can be used to align the areola markers such that they are equidistantly spaced from one another.

18 Claims, 9 Drawing Sheets

(56) References Cited

U.S. PATENT DOCUMENTS

| | | | | |
|---|---|---|---|---|
| 7,707,736 | B2* | 5/2010 | Keenan | A61B 17/32 33/566 |
| 8,064,987 | B2* | 11/2011 | Carr, Jr. | A61B 5/6842 600/431 |
| 8,594,768 | B2* | 11/2013 | Phillips | A61B 90/39 606/151 |
| 8,776,387 | B1* | 7/2014 | Butler-Ammar | G01B 3/34 33/555.2 |
| 8,832,955 | B2* | 9/2014 | Petter | A41H 1/02 33/759 |
| 9,277,963 | B2* | 3/2016 | Thompson | A61B 18/18 |
| 9,568,296 | B2* | 2/2017 | Moore | A61B 5/4312 |
| 9,858,611 | B2* | 1/2018 | Cooper | A41H 3/007 |
| 10,492,884 | B2* | 12/2019 | Ramos | A61B 90/39 |
| 11,406,489 | B2* | 8/2022 | Simmons | A61L 27/52 |
| 11,877,898 | B2* | 1/2024 | Alvarez | A61B 90/39 |
| 11,883,150 | B2* | 1/2024 | Greene | A61B 90/98 |
| 2009/0024225 | A1* | 1/2009 | Stubbs | A61L 31/148 623/23.72 |
| 2015/0216613 | A1* | 8/2015 | Schilling | A61B 5/6841 33/512 |
| 2020/0289153 | A1* | 9/2020 | Hurtak | A61B 17/3417 |
| 2022/0071608 | A1* | 3/2022 | Nock | A61B 90/39 |
| 2022/0071732 | A1* | 3/2022 | Rebellino | A61B 90/39 |
| 2022/0287795 | A1* | 9/2022 | Nomura | C09J 7/38 |

* cited by examiner

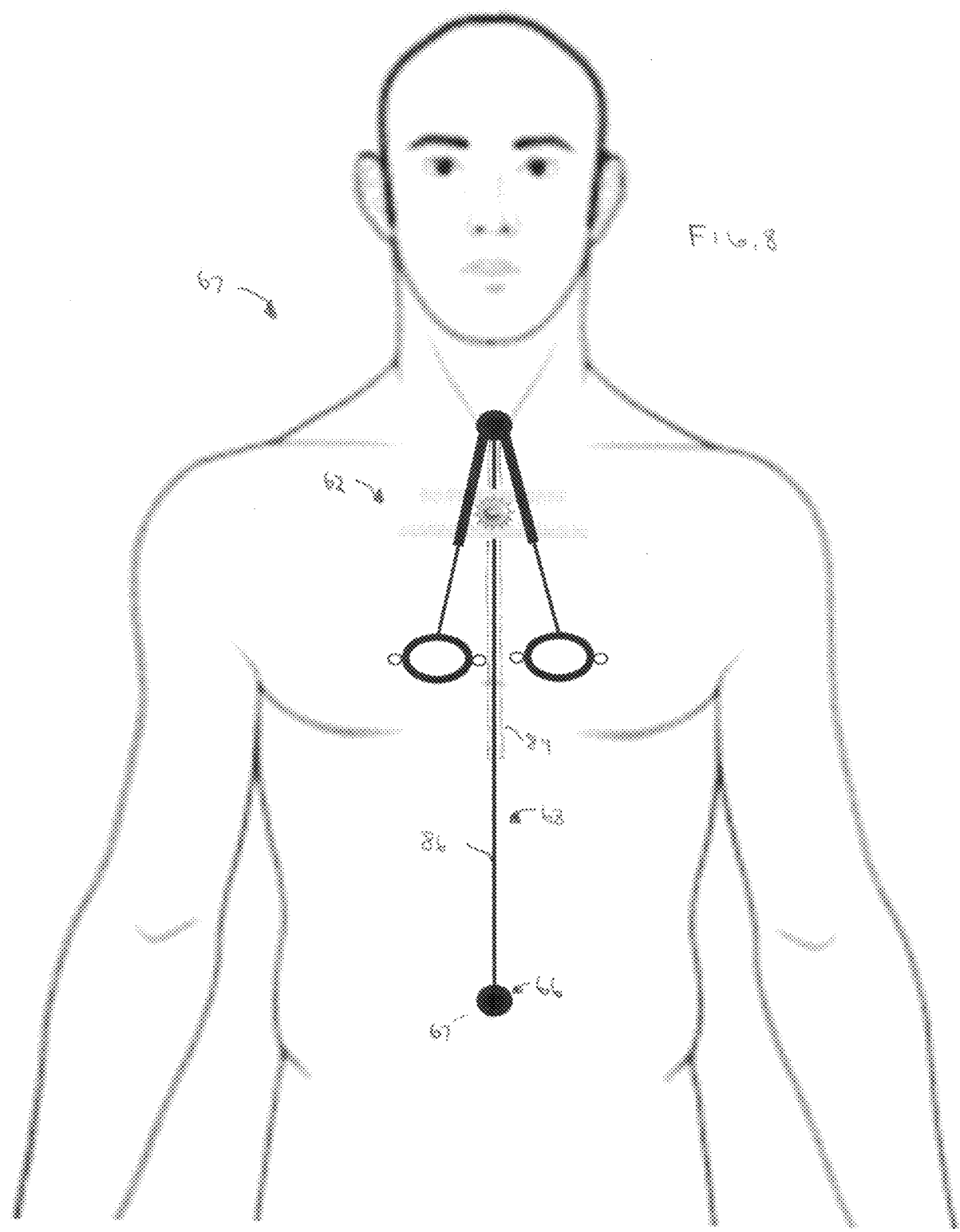

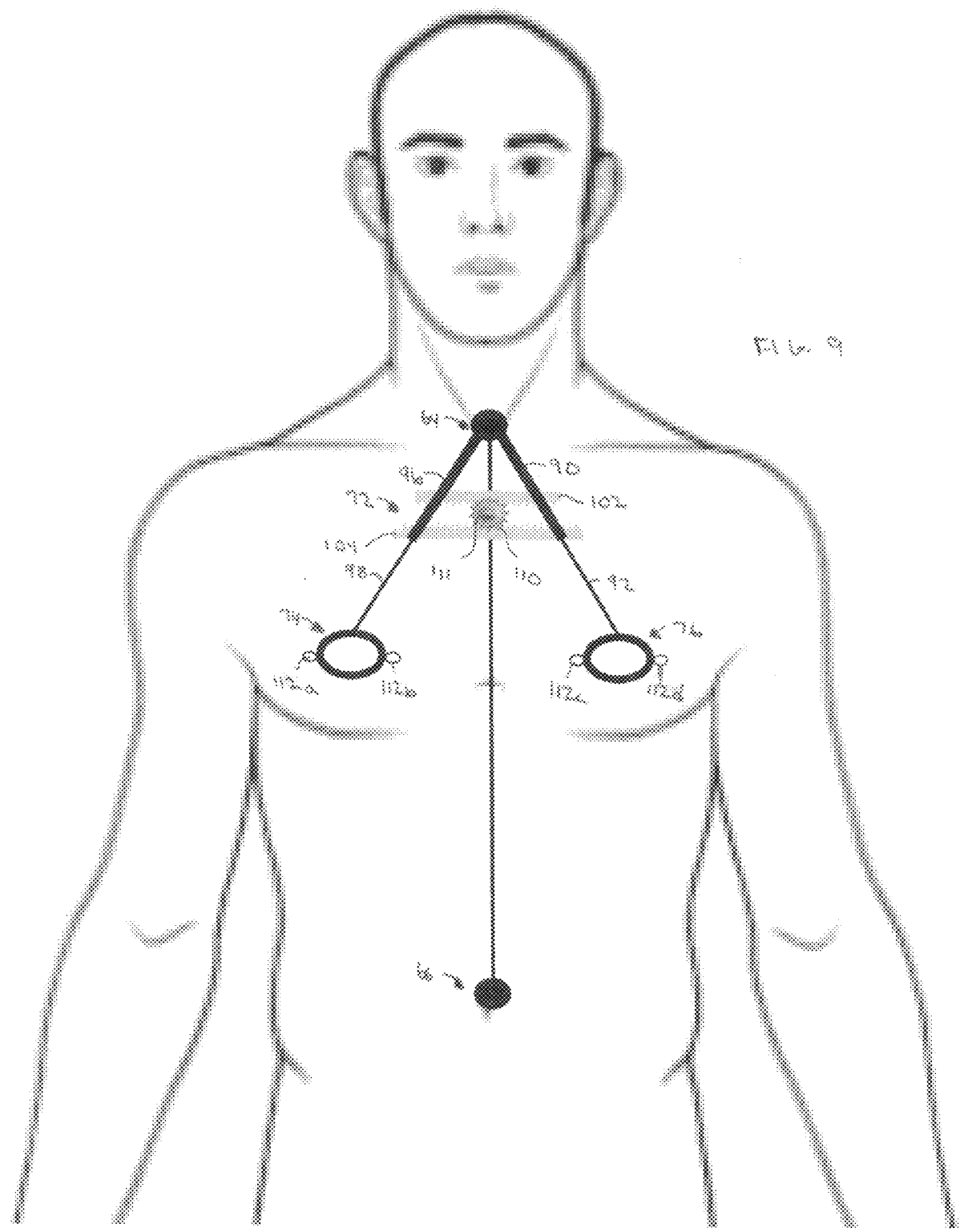

500
AREOLA MARKER PLACEMENT GUIDE

CROSS-REFERENCE TO RELATED APPLICATIONS

The present application claims priority to U.S. Provisional Application No. 63/176,592 filed on Apr. 19, 2021 and incorporated by reference in its entirety.

TECHNICAL FIELD

The present disclosure relates to an areola marker placement guide.

BACKGROUND

Chest masculinization surgery involves mastectomies and repositioning/reshaping of the nipple and areola to create a masculine contour and appearance to the chest. In particular, breast tissue and excess skin are removed from a female-to-male patient, and the chest and nipple areolar complex are reconstructed to appear masculinized. Depending on the size of the patient's chest, either a keyhole (subcutaneous mastectomy) or double incision (simple mastectomy) technique is utilized. In most cases, the nipple areolar complex is also resized, reshaped, and placed in a more masculine position, which is typically away from the central aspect of the breast mound.

SUMMARY

The present disclosure relates to areola marker placement guides. In an aspect, a guide can comprise a superior anchor and an inferior anchor. A slidable housing having a horizontal axis and a vertical axis can be located between the superior anchor and the inferior anchor. A vertical telescoping assembly can extend through the slidable housing along the vertical axis. The vertical telescoping assembly can include a top vertical arm connected to and extending downward from the superior anchor, a bottom vertical arm connected to and extending upward from the inferior anchor, and a vertical tube telescopically receiving the top vertical arm and the bottom vertical arm. The guide also can include a horizontal telescoping assembly extending from the slidable housing along the horizontal axis. The horizontal telescoping assembly can comprise a left horizontal telescoping assembly comprising a left horizontal arm having a lateral end connected to a left areolar marker and a left horizontal tube having a medial end connected to the slidable housing and telescopically receiving the left horizontal arm. The horizontal telescoping assembly also can include a right horizontal telescoping assembly. This assembly can include a right horizontal arm having a lateral end connected to a right areolar marker and a right horizontal tube having a medial end connected to the slidable housing and telescopically receiving the right horizontal arm.

In another aspect, an areola marker placement guide can comprise a superior anchor having a central axis and an inferior anchor. The guide also can include a central telescoping assembly comprising a central tube connected to and extending downward from the superior anchor along the central axis and a central arm telescopically received in the central tube and having an end connected to the inferior anchor. A lateral telescoping assembly can be pivotably connected to the superior anchor to pivot about the central axis of the superior anchor. The lateral telescoping assembly can comprise a left telescoping assembly and a right telescoping assembly. The left telescoping assembly can comprise a left tube connected to and extending downward from the superior anchor and a left arm telescopically received in the left tube. The right telescoping assembly can comprise a right tube connected to and extending downward from the superior anchor, and a right arm telescopically received in the right tube. The guide further can include an adjustment device configured to control lateral movement of the lateral telescoping assembly. The adjustment device can include a top rack connected to the left or the right telescoping assembly, a bottom rack connected to the other one of the left or the right telescoping assembly, and a pinion gear engaging the top and bottom racks. The guide further can include a left areola marker connected to an end of the left arm of the left telescoping assembly and a right areola marker connected to an end of the right arm of the right telescoping assembly.

BRIEF DESCRIPTION OF DRAWINGS

FIGS. 7-9 are frontal views of a patient schematically illustrating different steps during use of an areola marker placement guide according to an aspect of the present disclosure.

DETAILED DESCRIPTION

The present invention relates to an areola marker placement guide. As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the shape, configuration, or direction of the described element need not have the mathematically exact described shape, configuration, or direction of the described element but can have a shape, configuration, or direction that is recognizable by one skilled in the art as generally or approximately having the described shape, configuration or direction of the described element. As such "substantially" refers to the complete or nearly complete extent of a characteristic. The exact allowable degree of deviation from the characteristic will be so as to have the same overall result as if the absolute characteristic were obtained. The terms "left," "right," "top," "bottom," "inferior," "superior," "lateral," and "medial" are with reference to a patient in a standard anatomical position and not necessarily with respect to the figures (such as FIGS. 2, 3, 5 and 6). By "integral" or "integrated" is meant that the described components are fabricated as one piece or multiple pieces affixed during manufacturing such that the components are a unitary and continuous piece after manufacturing. Such described components are not separable without damaging the integrity (i.e. tearing) of either of the components as opposed to two-piece or multi-piece components that are assembled together after manufacturing, such as prior to or during surgical insertion, and where the components can be separated or are meant to be separated. As used herein a "patient" includes a mammal such as a human being. All device, assemblies, and kits as described herein are used for medical purposes and are therefore sterile.

Figure 1:
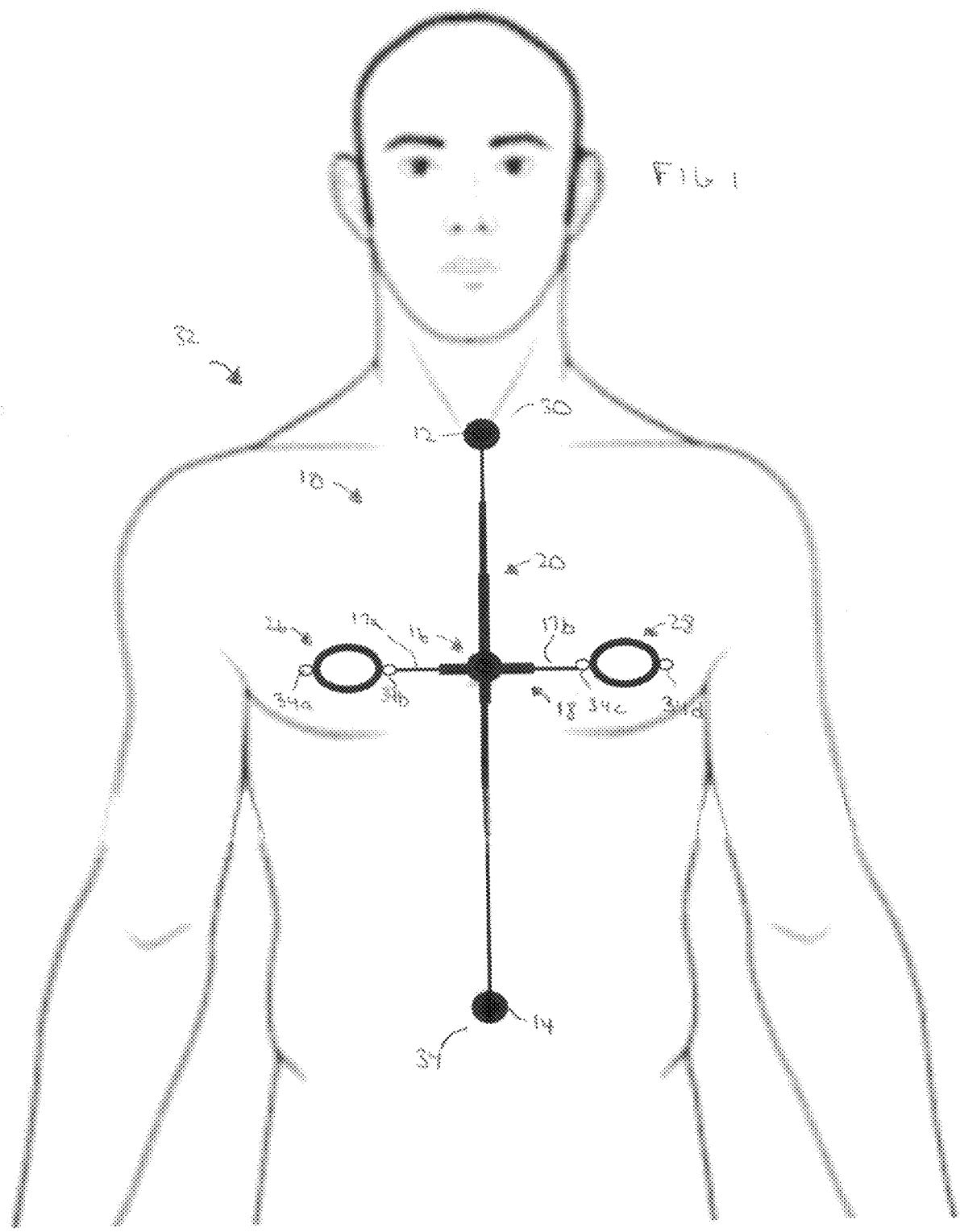
FIG. 1 is a frontal view of a patient schematically illustrating an areola marker placement guide placed on the patient according to an aspect of the present disclosure.

Referring to FIG. 1, in an aspect, an areola marker placement guide 10 can comprise a superior anchor 12, an inferior anchor 14, a slidable housing 16 located between superior and inferior anchors 12 and 14, a vertical telescoping assembly 20 extending through slidable housing 16, a horizontal telescoping assembly 18 extending from slidable housing 16, and areola markers 26 and 28 connected to the horizontal telescoping assembly 18.

Superior anchor 12 can be sized and dimensioned to fit in the jugular notch 30 of patient 32's sternum, for example, as illustrated in FIG. 1. Although the superior anchor is illustrated as being substantially circular in shape, it can have other configurations so long as it can be fixated to an anatomical location above the areola markers. Inferior anchor 14 can be sized and dimensioned to fit in the navel 34 of patient 32, for example, as illustrated in FIG. 1. As with the superior anchor, although the inferior anchor is illustrated as being substantially circular in shape, it can have other configurations so long as it can be fixated to an anatomical location below the areola markers.

Areola marker placement guide has a vertical axis Y that extends through slidable housing 16 and through vertical telescoping assembly 20. The guide also has a horizontal axis X that extends through slidable housing 16, horizontal telescoping assembly 18 and areola markers 26 and 28 as identified in FIG. 2. As schematically depicted in FIG. 3, slidable housing 16 can slide along vertical axis Y to move in an inferior/superior direction (shown in shadow in FIG. 3 and as depicted by arrow 19). Although housing 16 is illustrated as being substantially circular in shape, it can have other configurations so long as it capable of performing its functionality as described herein.

Figure 2:
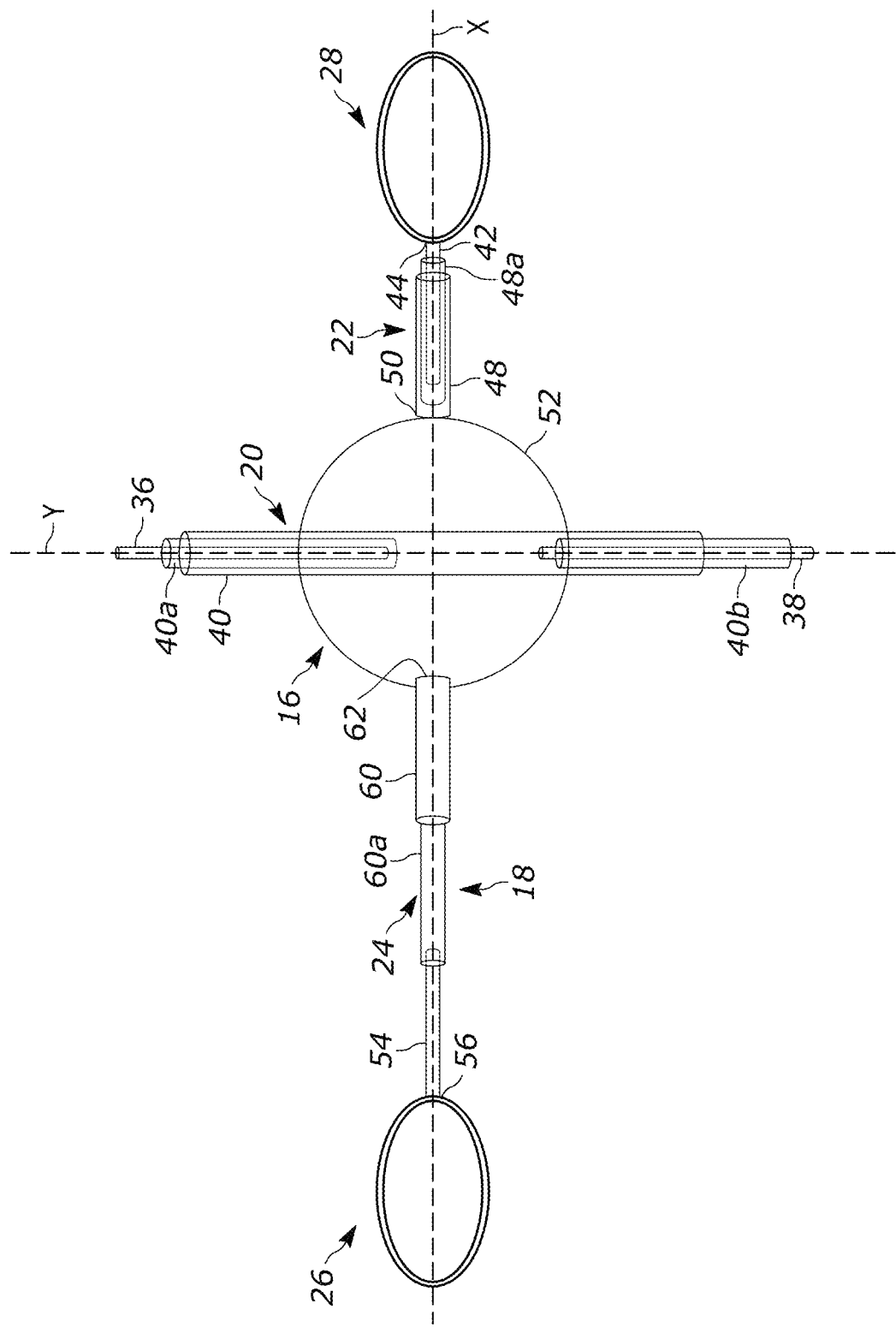
FIG. 2 is a perspective view of components of the areola marker placement guide of FIG. 1.
Figure 3:
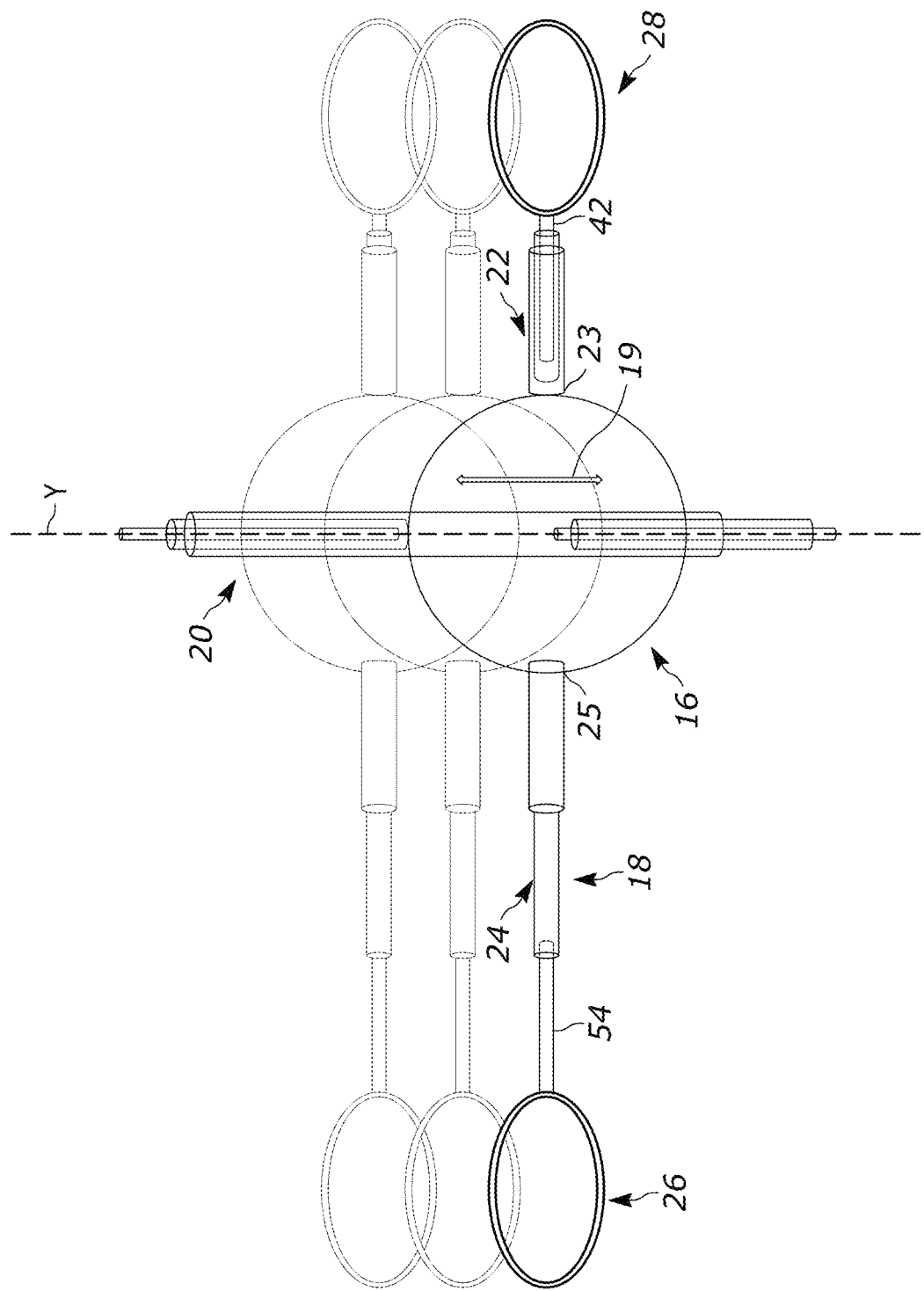
FIG. 3 is a perspective view of components of the areola marker placement guide of FIG. 2 schematically depicting movement of the slidable housing of FIG. 3 along the vertical telescoping assembly in a superior/inferior direction.
Figure 4:
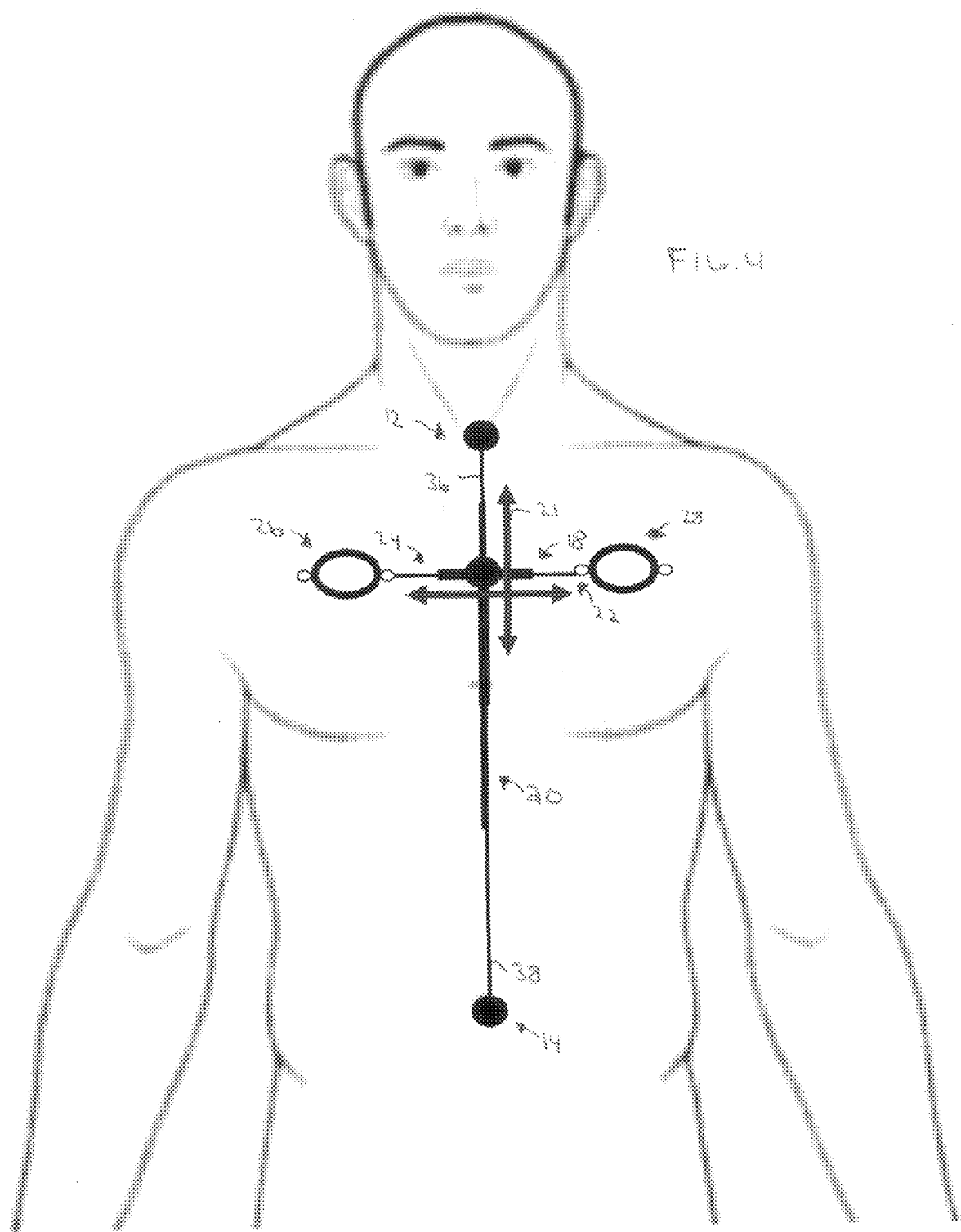
FIG. 4 is a frontal view of a patient schematically illustrating an areola marker placement guide placed on the patient according to an aspect of the present disclosure where the slidable housing is shown in a superior position compared to FIG. 1.

Referring to FIG. 2-4, vertical telescoping assembly 20 can extend through slidable housing 16 along vertical axis Y. It should be noted that the verticality of telescoping assembly 20 and components thereof can be vertical or substantially vertical with respect to the slidable housing and the term "vertical" encompasses minor deviations such that telescoping assembly 20 would be understood by one skilled in the art as extending in a vertical direction with respect to the slidable housing. Vertical telescoping assembly 20 can comprise a top vertical arm 36 connected to and extending downward from superior anchor 12 and a bottom vertical arm 38 extending upward from inferior anchor 14. The vertical arms can be non-releasably or releasably attached to the respective anchor. A vertical tube 40 can telescopically receive top vertical arm 36 and bottom vertical arm 38 either directly or via an intermediate tube(s). Both top vertical arm 36 and bottom vertical arm 38 can move independent of one another in a respective superior and inferior direction as indicated by arrow 21.

Horizontal telescoping assembly 18 can extend from slidable housing, such as from an outer surface 52 of slidable housing 16, along horizontal axis X. It should be noted that the horizontality of telescoping assembly 18 and components thereof can be horizontal or substantially horizontal with respect to the slidable housing and the term "horizontal" encompasses minor deviations such that horizontal telescoping assembly 18 would be understood by one skilled in the art as extending in a horizontal direction with respect to the slidable housing. Horizontal telescoping assembly 18 can comprise a left horizontal telescoping assembly 22 and a right horizontal telescoping assembly 24. Left horizontal telescoping assembly 22 can comprise a left horizontal arm 42 having a lateral end 44 connected to left areolar marker 28 and a left horizontal tube 48 having a medial end 50 connected to the outer surface 52, for example, of slidable housing 16 and telescopically receiving left horizontal arm 42 either directly or via an intermediate tube(s). Right horizontal assembly 24 can include a right horizontal arm 54 having a lateral end 56 connected to right areolar marker 26 and a right horizontal tube 60 having a medial end 62 connected to slidable housing 16 and telescopically receiving right horizontal arm 54 either directly or via an intermediate tube(s). For example, the medial ends of the left and right horizontal tubes can be fused or otherwise non-releasably connected to the slidable housing, such as the outer surface 52 of the slidable housing at sites 23 and 25.

Figure 5:
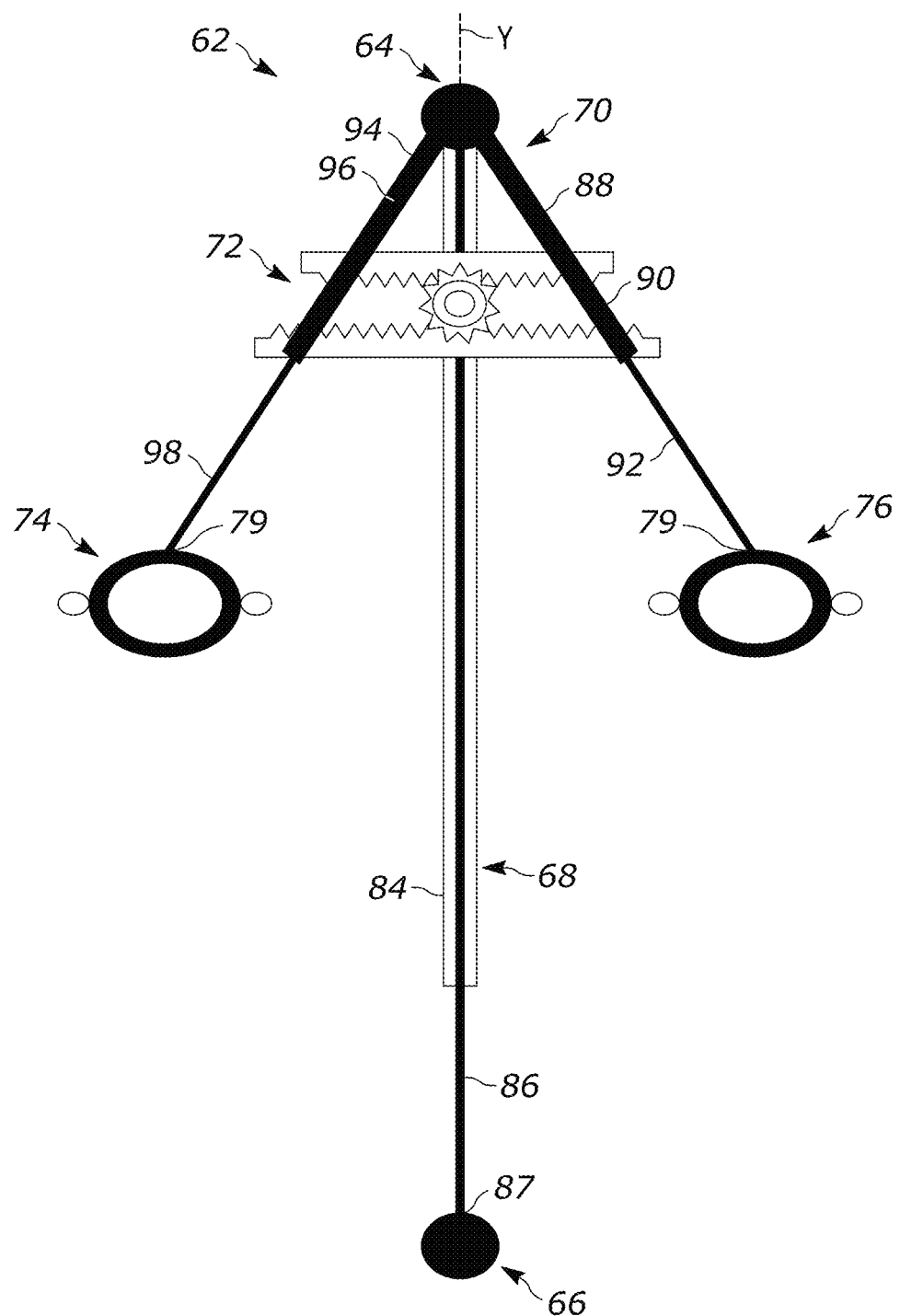
FIG. 5 is a side view of an areola marker placement guide according to an aspect of the present disclosure.

Referring to FIG. 5, in an aspect an areola marker placement guide 62 can include a superior anchor 64, an inferior anchor 66, a central telescoping assembly 68, a lateral telescoping assembly 70, an adjustment device 72, and areola markers 74 and 76. Superior anchor 64 can have a central axis Y and can be sized and dimensioned to fit into an anatomical location above the areola markers, such as the jugular notch of the patient's sternum. Inferior anchor 66 can be sized and dimensioned to fit into an anatomical below the areola markers, such as the naval of the patient. Both the superior and the inferior anchor can have suitable configurations, such as for example, ring-shaped, to fit into the appropriate anatomical location.

Central telescoping assembly 68 can include a central tube 84 connected to and extending downward from superior anchor 64 along central axis Y. A central arm 86 can be telescopically received in central tube 84 and can have an inferior end 87 connected to inferior anchor 66. It should be noted that the centrality of telescoping assembly 68 and components thereof can be central or substantially central relative to the superior anchor and the term "central" encompasses such minor deviations such that telescoping assembly 68 would be understood by one skilled in the art as extending from the center of the superior anchor.

Lateral telescoping assembly 70 can be pivotably connected to superior anchor 64 via a hinge or other pivot mechanism to pivot about the central axis Y of superior anchor 64. This allows for lateral movement and positioning of the central telescoping assembly prior to anchoring of the assembly. Lateral telescoping assembly 70 can include a left telescoping assembly 88 comprising a left tube 90 connected to and extending downward from superior anchor 64 and a left arm 92 telescopically received in left tube 90. Lateral telescoping assembly 70 can further include a right telescoping assembly 94 comprising a right tube 96 connected to and extending downward from superior anchor 64 and a right arm 98 telescopically received in right tube 96.

Figure 6:
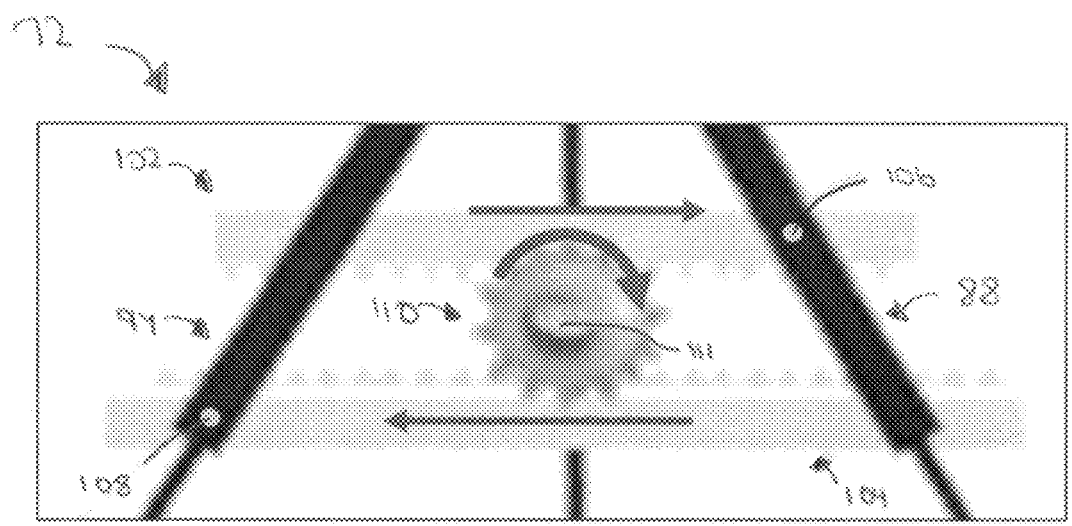
FIG. 6 is a side enlarged view of the adjustment device of the areola marker placement guide of FIG. 5.

Referring to FIG. 6, adjustment device 72 can be configured to control lateral movement of lateral telescoping assembly 70 and can comprise a top rack 102 connected to the left or the right telescoping assembly and a bottom rack 104 connected to the other one of the left or the right telescoping assembly. FIG. 6 illustrates a pin 106 connecting top rack 102 to left telescoping assembly 88 and a pin 108 connecting bottom rack 104 to right telescoping assembly 94 but the top rack could be connected to the right telescoping assembly and the bottom rack could be connected to the left telescoping assembly. A pinion gear 110 can engage the top and bottom rack 102 and 104 and can include a knob 111 on a front surface thereof. Turning the knob can result in the right and left telescoping assemblies moving laterally (as indicated by the arrows) to the same extent such that the areola markers are equidistant from the central telescoping assembly.

Referring back to FIG. 5, a left areola marker 76 can be connected to an end 77 of left arm 92 of left telescoping assembly 88. A right areola marker 74 can be connected to an end 79 of right arm 98 of right telescoping assembly 94. The areola markers can be specifically designed for chest masculinization procedures.

The areola markers can be releasably or non-releasably connected to respective telescoping arms. By being releasably connected, areola markers of different sizes and dimensions can be used with the placement guide. For example, the areola markers can be oval shaped with a horizontal major axis. The placement guide can be used with areola markers having different major diameters. For example, different diameters of areola markers can be utilized starting, for example, at a diameter of 18×14 mm. Markers can be part of a set of five, for example, having 0.1 mm increments. As such, kits are provided herein that include an areola marker placement guide and areola markers as described herein. The markers can have a circumference diameter ranging from about 18 mm to 23 mm for handling and grip over the patient's body surface. The markers can be fabricated from a metal or plastic, such as stainless steel, for example. The sized of the markers can be engraved on the inner surface of the markers such as engraved or otherwise printed at the 3:00, 6:00, 9:00, and 12:00 position to guide rotation of the device. The areola markers can also include suture rings 34a-d as depicted in FIG. 1 in order to fixate the areola markers in place. Although four suture rings are included more or less suture rings can be provided so long as the areola markers can be fixed in place.

Although the various telescoping assemblies described above can include a single outer tube and an inner arm telescopically received by the single outer tube, telescopically assemblies can include nested tubes. For example, FIGS. 2 and 3 depict a vertical telescoping assembly with a vertical tube 40 and additional nested top tube 40a and nested bottom tube 40b, the nesting tubes each having a diameter less than the diameter of vertical tube 40 but greater than the diameter of respective vertical arms 36 and 38 and such that vertical arms 36 and 38 are telescopically received within tubes 40a and 40b respectively.

Similarly, FIGS. 2 and 3 depict a horizontal telescoping assembly with a left horizontal telescoping assembly including a left horizontal tube 48 and an additional left horizontal tube 48a nested within tube 48. Similarly, the right telescoping assembly includes a right horizontal tube 60 and an additional right horizontal tube 60a nested within tube 60. The diameters of tube 48a and tube 60a can each have a diameter less than the diameter of respective tube 48 and 60 but greater than the diameter of respective left and right arms 42 and 54 such that arms 42 and 54 are telescopically received within tubes 48a and 60a respectively.

Irrespective of the number of nested tubes, the tube(s) can telescopically receive the respective arm(s) via friction, push buttons, set screws or other telescoping mechanisms. For example, the medial end of a telescoping arm can be crimped or angled inward against the tube through which it telescopes to create friction against the tube. As indicated by FIG. 1, the telescoping assemblies can have ruler markings 17 thereon, such as on the telescoping arms, to accurately adjust the distance between the left and right areola markers. Such ruler markings allow for equal distancing of the right and left areola markers.

Figure 7:
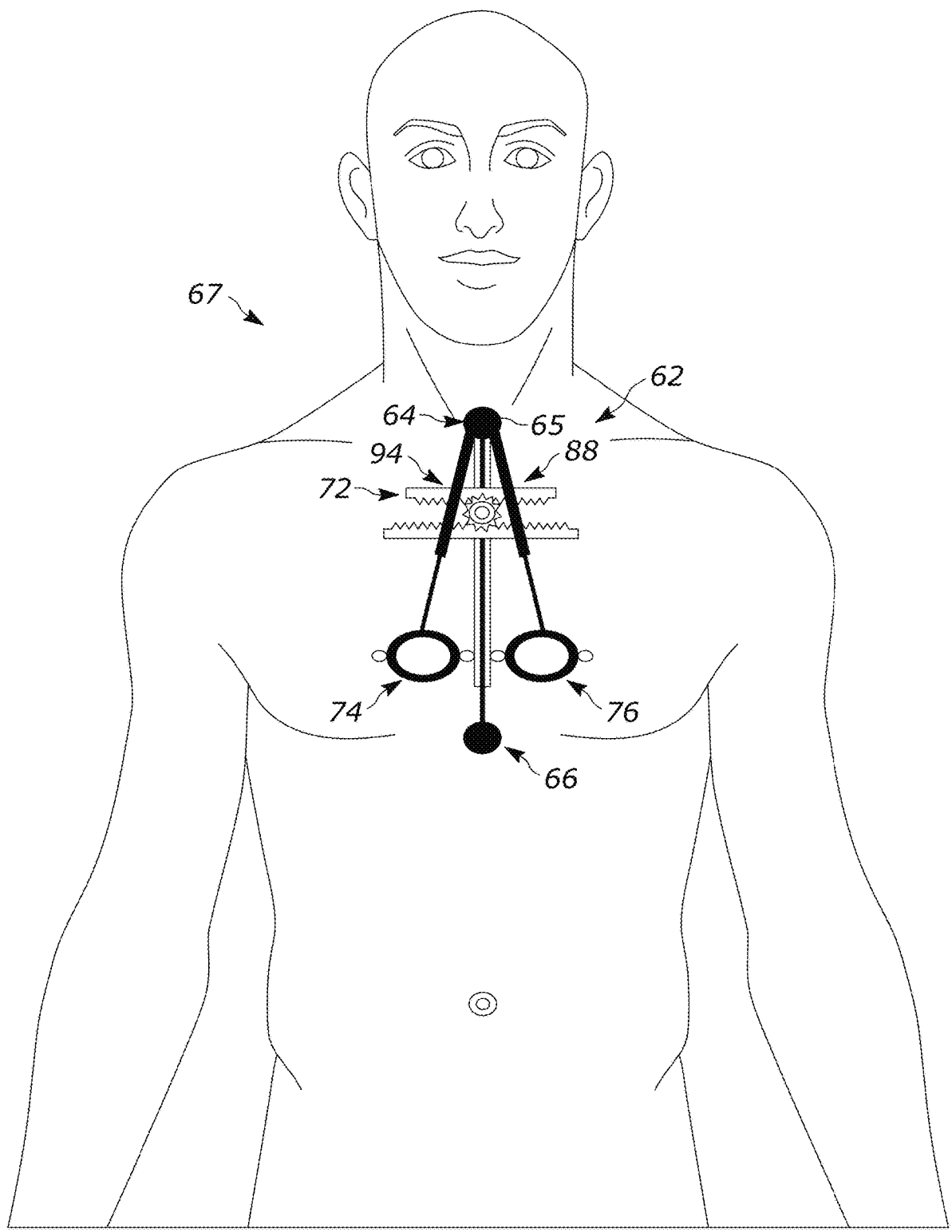

An exemplary method of using an areola marker placement guide will now be described with respect to FIGS. 7-9. Superior anchor 64 is secured in the jugular notch 65 of the patient 67. Central arm 86 of central telescoping assembly 68 can be extended downwards from central tube 84 and inferior anchor 66 can be secured in the naval 67. Knob 111 of pinion gear 110 can be rotated until respective left and right areola markers 76 and 74 are correctly positioned. The areola markers are then sutured to the patient through anchor rings 112a-112d.

Although the drawings show certain elements of an areolar marker placement guide and kit in combination, it should be noted that such elements can be included in other embodiments or aspects illustrated in other drawings or otherwise described in the specification. In other words, each of the disclosed aspects and embodiments of the present disclosure may be considered individually or in combination with other aspects and embodiments of the disclosure including patent applications incorporated by reference herein. Additionally, when describing a range, all points within that range are included in this disclosure. Further, unless otherwise specified, none of the steps of the methods of the present disclosure are confined to any particular order of performance.

What is claimed is:
1. An areola marker placement guide comprising:
a superior anchor;
an inferior anchor;
a slidable housing having a horizontal axis and a vertical axis and located between the superior anchor and the inferior anchor;
a vertical telescoping assembly extending through the slidable housing along the vertical axis and comprising:
a top vertical arm connected to and extending downward from the superior anchor;
a bottom vertical arm connected to and extending upward from the inferior anchor; and
a vertical tube telescopically receiving the top vertical arm and the bottom vertical arm; and
a horizontal telescoping assembly extending from the slidable housing along the horizontal axis and comprising:
a left horizontal telescoping assembly comprising:
a left horizontal arm having a lateral end connected to a left areolar marker; and
a left horizontal tube having a medial end connected to the slidable housing and telescopically receiving the left horizontal arm;
a right horizontal telescoping assembly comprising:
a right horizontal arm having a lateral end connected to a right areolar marker; and
a right horizontal tube having a medial end connected to the slidable housing and telescopically receiving the right horizontal arm.

2. The areola marker placement guide of claim 1, further comprising at least one suture anchor ring coupled to each of the left and right areola markers.

3. The areola marker placement guide of claim 1, wherein the superior anchor is sized and dimensioned to fit in the jugular notch.

4. The areola marker placement guide of claim 1, wherein the inferior anchor is sized and dimensioned to fit in the navel.

5. The areola marker placement guide of claim 1, wherein the right and left horizontal arms have ruler markings thereon.

6. The areola marker placement guide of claim 1, wherein the left areola marker is releasably connected to an end of the left arm of the left telescoping assembly and the right areola marker is releasably connected to an end of the right arm of the right telescoping assembly.

7. The areola marker placement guide of claim 6, wherein the right and the left areola markers are oval shaped with a horizontal major axis.

8. A kit comprising:
the areola marker placement guide of claim 1; and
a plurality of areola markers having different major diameters.

9. The areola marker placement guide of claim 1, wherein the left horizontal tube and the right horizontal tube are connected to the outer surface of the slidable housing.

10. An areola marker placement guide comprising:
a superior anchor having a central axis;
an inferior anchor;
a central telescoping assembly comprising:
   a central tube connected to and extending downward from the superior anchor along the central axis; and
   a central arm telescopically received in the central tube and having an end connected to the inferior anchor;
a lateral telescoping assembly pivotably connected to the superior anchor to pivot about the central axis of the superior anchor and comprising:
   a left telescoping assembly comprising:
      a left tube connected to and extending downward from the superior anchor; and
      a left arm telescopically received in the left tube; and
   a right telescoping assembly comprising:
      a right tube connected to and extending downward from the superior anchor; and
      a right arm telescopically received in the right tube;
an adjustment device configured to control lateral movement of the lateral telescoping assembly and comprising:
   a top rack connected to the left or the right telescoping assembly;
   a bottom rack connected to the other one of the left or the right telescoping assembly;
   a pinion gear engaging the top and bottom racks;
a left areola marker connected to an end of the left arm of the left telescoping assembly; and
a right areola marker connected to an end of the right arm of the right telescoping assembly.

11. The areola marker placement guide of claim 10, further comprising at least one suture anchor ring coupled to each of the left and right areola markers.

12. The areola marker placement guide of claim 10, wherein the superior anchor is sized and dimensioned to fit in the jugular notch.

13. The areola marker placement guide of claim 10, wherein the inferior anchor is sized and dimensioned to fit in the navel.

14. The areola marker placement guide of claim 10, wherein the right and left arms have ruler markings thereon.

15. The areola marker placement guide of claim 10, wherein the left areola marker is releasably connected to an end of the left arm of the left telescoping assembly and the right areola marker is releasably connected to an inferior end of the right arm of the right telescoping assembly.

16. The areola marker placement guide of claim 15, wherein the right and the left areola markers are oval shaped with a horizontal major axis.

17. A kit comprising:
the areola marker placement guide of claim 10; and
a plurality of areola markers having different major diameters.

18. The areola marker of claim 10, wherein a front face of the pinion gear comprises a knob.

* * * * *